(12) United States Patent
Azhakanandam et al.

(10) Patent No.: US 9,068,191 B2
(45) Date of Patent: Jun. 30, 2015

(54) METHODS AND COMPOSITIONS FOR A SOYBEAN IN-PLANTA TRANSIENT EXPRESSION SYSTEM

(75) Inventors: Kasimalai Azhakanandam, Durham, NC (US); Pei Su, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 617 days.

(21) Appl. No.: 13/326,786

(22) Filed: Dec. 15, 2011

(65) Prior Publication Data
US 2012/0174262 A1 Jul. 5, 2012

Related U.S. Application Data

(60) Provisional application No. 61/427,935, filed on Dec. 29, 2010.

(51) Int. Cl.
C12N 15/84 (2006.01)
C12N 15/87 (2006.01)
C12N 15/82 (2006.01)

(52) U.S. Cl.
CPC ........ *C12N 15/8205* (2013.01); *C12N 15/8202* (2013.01); *C12N 15/8207* (2013.01); *C12N 15/8216* (2013.01); *C12N 15/8257* (2013.01)

(58) Field of Classification Search
None
See application file for complete search history.

(56) References Cited

U.S. PATENT DOCUMENTS

| 5,276,268 | A | 1/1994 | Strauch et al. |
| 6,573,428 | B1 | 6/2003 | Vodkin et al. |
| 7,723,570 | B2 * | 5/2010 | Piller et al. ............... 800/288 |
| 2006/0051870 | A1 | 3/2006 | Held et al. |
| 2009/0049567 | A1 | 2/2009 | Olhoft et al. |

FOREIGN PATENT DOCUMENTS

WO    WO 00/58484 A2    10/2000

OTHER PUBLICATIONS

Burghardt et al. J. Agric. Food Chem. 46: 1593-1706 (1998).*
Somleva et al. Crop Science 42(6): 2080-2087 (2002).*
D'Aoust et al. Plant Biotechnology Journal 6: 930-940 (2008).*
Schob et al. Molecular and General Genetics 256: 581-585 (1997).*
Notification Concerning Transmittal of International Preliminary Report on Patentability mailed on Jul. 2, 2013 in corresponding PCT Application No. PCT/US2011/065092 (8 pages).
Balestra, G.M. et al., "Increased Susceptibility to *Pseudomonas syringae* pv. *syringae* and *Pseudomonas viridiflava* of Kiwi Plants having Transgenic rolABC genes and its Inheritance in the T1 Offspring", *J. Phytopathology*, vol. 149, 2001, pp. 189-194.
Clergeot, Pierre-Henri et al., "PLS1, a gene encoding a tetraspanin-like protein, is required for penetration of rice leaf by the fungal pathogen *Magnaporthe grisea*", *PNAS*, Jun. 5, 2001, vol. 98, No. 12, pp. 6963-6968.
Clough, Steven J. et al., "Floral dip: a simplified method for Agrobacterium-mediated transformation of *Arabidopsis thaliana*", *The Plant Journal*, vol. 16, No. 6, 1998, pp. 735-743.
Curtis I.S. et al., "Transgenic radish (*Raphanus sativus* L. *longipinnatus* Bailey) by floral-dip method—plant development and surfactant are important in optimizing transformation efficiency", *Transgenic Research*, vol. 10, 2001, pp. 363-371.
DeGray, Gerald et al., "Expression of an Antimicrobial Peptide via the Chloroplast Genome to Control Phytopathogenic Bacteria and Fungi", *Plant Physiology*, Nov. 2001, vol. 127, pp. 852-862.
Furini, Antonella et al., "Agrobacterium-mediated transformation of the desiccation-tolerant plant *Craterostigma plantagineum*", *Plant Cell Reports*, vol. 14, 1994, pp. 102-106.
Giddix Jr., L.R. et al., "Effect of Light on Bacteria-Induced Hypersensitivity in Soybean", *Phytopathology*, vol. 71, No. 2, 1981, pp. 111-115.
Hoshi Y. et al., "Production of transgenic lily plants by Agrobacterium-mediated transformation", *Plant Cell Rep*, vol. 22, 2004, pp. 359-364.
International Search Report Corresponding to International PCT/US11/65092; Date of Mailing: Apr. 6, 2012; 11 pages.
Jones, Susan B. et al., "Fate of *Xanthomonas campestris* Infiltrated into Soybean Leaves: An Ultrastructural Study", *Phytopathology*, vol. 75, No. 6, 1985, pp. 733-741.
Kapila, Jyoti et al., "An Agrobacterium-mediated transient gene expression system for intact leaves", *Plant Science*, vol. 122, 1997, pp. 101-108.
Liu, Sheng-Jun et al., "The effect of co-cultivation and selection parameters on Agrobacterium-mediated transformation of Chinese soybean varieties", *Plant Cell Rep*, vol. 27, 2008, pp. 489-498.
Manavella, Pablo A. et al., "Transient transformation of sunflower leaf discs via an Agrobacterium-mediated method: applications for gene expression and silencing studies", *Nature Protocols*, vol. 4, No. 11, 2009, pp. 1699-1707.
Simmons, Christopher W. et al., "A Model of *Agrobacterium tumefaciens* Vacuum Infiltration Into Harvested Leaf Tissue and Subsequent in Planta Transgene Transient Expression", *Biotechnology and Bioengineering*, vol. 102, No. 3, Feb. 15, 2009, pp. 965-970.

(Continued)

*Primary Examiner* — David T Fox
(74) *Attorney, Agent, or Firm* — Yoshimi D. Barron

(57) ABSTRACT

This invention provides methods of transiently expressing a nucleotide sequence in one or more cells of a soybean plant, comprising: a) abrading the surface of a soybean plant and/or intact part thereof; and either (b1) immersing the abraded plant and/or abraded intact part thereof in a solution comprising *Agrobacterium* cells and a surfactant, wherein the *Agrobacterium* cells comprise the nucleotide sequence to be transiently expressed; (b2) applying a vacuum to the immersed soybean plant and/or intact part thereof of step (b1); and (b3) releasing the vacuum, thereby introducing the solution into the plant and/or intact part thereof; or (c) contacting the abraded plant and/or abraded intact part thereof with a solution comprising *Agrobacterium* cells and a surfactant, wherein the *Agrobacterium* cells comprise the nucleotide sequence to be transiently expressed, whereby the nucleotide sequence is transiently expressed in one or more cells of the plant.

10 Claims, No Drawings

(56) References Cited

OTHER PUBLICATIONS

VanderGheynst, J.S. et al., "Response surface studies that elucidate the role of infiltration conditions on *Agrobacterium tumefaciens*-mediated transient transgene expression in harvested switchgrass (*Panicum virgatum*)", *Biomass and Bioenergy*, vol. 32, 2008, pp. 372-379.

Yamada, Tetsuya et al., "Cotyledonary node pre-wounding with a micro-brush increased frequency of Agrobacterium-mediated transformation in soybean", *Plant Biotechnology*, vol. 27, 2010, pp. 217-220.

Yang, Aifang et al., "Improvement of Agrobacterium-Mediated Transformation of embryogenic Calluses From Maize Elite Inbred Lines", *In Vitro Cellular and Developmental Biology.—Plant*, vol. 42, May-Jun. 2006, pp. 215-219.

* cited by examiner

METHODS AND COMPOSITIONS FOR A SOYBEAN IN-PLANTA TRANSIENT EXPRESSION SYSTEM

STATEMENT OF PRIORITY

This application claims the benefit, under 35 U.S.C. §119(e), of U.S. Provisional Application No. 61/427,935; filed Dec. 29, 2010, the entire contents of which is incorporated by reference herein.

FIELD OF THE INVENTION

The present invention provides methods related generally to the expression of nucleic acids in plants. Specifically, this invention relates to methods and compositions for transient expression of nucleotide sequences in an intact soybean plant and/or part thereof.

BACKGROUND OF THE INVENTION

Soybean is one of the most important commercial crops world-wide. The ability to evaluate genetic elements along with nucleotide sequences of interest is important to the development of soybean plants with improved agronomic traits. However, evaluation and testing of genetic elements in stably transformed soybean plants is time and resource intensive. In contrast, evaluation of genetic elements using transient expression systems can be done in several days for far less cost.

Several viral based in-planta transient systems have been reported for soybean (Zhang and Ghabrial, *Virology* 344:401-11 (2006); Wang et al., *MPMI* 19:304-312 (2006); Zhang et al., *MPMI* 22:123-131 (2009); Zhang et al., *Plant Physiol.* 153:52-65 (2010); Yamagishi and Yoshikawa, *Plant Mol Biol.* 71:15-24 (2009). While viral-based transient transformation systems are useful for systemic and high level expression of nucleotide sequences of interest, viral-based transient transformation systems are less useful for evaluating genetic elements such as enhancers, promoters, whole expression cassettes, viral genes, and any genetic element that is larger than 2-3 kb. Expression of multiple genes/traits is commonly desired. Such constructs can be quite large, (e.g., 5-25 kb) and generally cannot be tested in plants using known viral systems.

Accordingly, the present invention addresses previous shortcomings in the art by providing compositions and methods for transiently expressing a nucleotide sequence in a soybean plant using binary vectors.

SUMMARY OF THE INVENTION

One aspect of the present invention provides a method of transiently expressing a nucleotide sequence in one or more cells of a soybean plant, comprising: a) abrading the surface of a soybean plant and/or intact part thereof; b) immersing the abraded soybean plant and/or abraded intact part thereof in a solution comprising bacterial cells competent for nucleic acid transfer and a surfactant, wherein the bacterial cells comprise the nucleotide sequence to be transiently expressed and a surfactant, wherein the bacterial cells comprise the nucleotide sequence to be transiently expressed; c) applying a vacuum to the immersed soybean plant and/or intact part thereof of step (b); and d) releasing the vacuum, thereby introducing the solution into the soybean plant and/or intact part thereof, whereby the nucleotide sequence is transiently expressed in one or more cells of the soybean plant.

A further aspect of the present invention provides a method of transiently expressing a nucleotide sequence in one or more cells of a soybean plant, comprising: a) abrading the surface of a soybean plant and/or intact part thereof; and b) contacting the abraded soybean plant and/or abraded intact part thereof with a solution comprising bacterial cells competent for nucleic acid transfer and a surfactant, wherein the bacterial cells comprise the nucleotide sequence to be transiently expressed and a surfactant, wherein the bacterial cells comprise the nucleotide sequence to be transiently expressed, whereby the nucleotide sequence is transiently expressed in one or more cells of the soybean plant.

In some aspects of the invention, the soybean plant or intact part thereof is contacted with alcohol prior to abrading the surface of the plant or intact part thereof. Further aspects of the present invention provide transiently transformed soybean plants made by the methods described herein.

In other aspects of the invention a method of predicting the expression of one or more nucleotide sequences in a stably transformed soybean plant is provided, comprising: transiently expressing the one or more nucleotide sequences in one or more cells of a soybean plant by the method of the present invention; and determining the level of expression of the one or more nucleotide sequences, wherein the level of expression determined in the transiently transformed soybean plant predicts the level of expression in a soybean plant stably transformed with said one or more nucleotide sequences.

In additional aspects of the invention a method of optimizing the expression of one or more nucleotide sequences in a soybean plant, comprising: (a) transiently expressing the one or more nucleotide sequences in one or more cells of a soybean plant by the methods of the present invention; (b) determining the level of expression of the one or more nucleotide sequences in the one or more cells of the transiently transformed soybean plant of step (a); (c) modifying at least one of the one or more nucleotide sequences to optimize the expression of the one or more nucleotide sequences in a soybean plant; (d) transiently expressing the one or more nucleotide sequences of step (c) in one or more cells of a soybean plant by the methods of the present invention; (e) determining the level of expression of the one or more nucleotide sequences of the transiently transformed soybean plant of step (d); and either, (f) verifying that the level of expression of the one or more nucleotide sequences is optimized; or (g) repeating steps (c) through (e) one or more limes and then verifying that the level of expression of the one or more nucleotide sequences is optimized, thereby optimizing the level of expression of the one or more nucleotide sequences in a soybean plant.

In still further aspects of the present invention, a method of producing a stably transformed soybean plant comprising one or more nucleotide sequences optimized for expression in a soybean plant, comprising, (a) transiently expressing one or more nucleotide sequences in one or more cells of a soybean plant by the methods of the present invention; (b) determining the level of expression of the one or more nucleotide sequences of the nucleic acid molecule in the one or more cells of the transiently transformed soybean plant of step (a); (c) modifying at least one of the one or more nucleotide sequences to optimize the expression of said one or more nucleotide sequences in a soybean plant; (d) transiently expressing the one or more nucleotide sequences of step (c) in one or more cells of a soybean plant according to the methods of the present invention; (e) determining the level of expression of the one or more nucleotide sequences of the transiently transformed soybean plant of step (d); then either, (f) verifying that the level of expression of the one or more nucleotide sequences is optimized; or (g) repeating steps (c) through (e) one or more times and then verifying that the level of expression of the one or more nucleotide sequences is optimized; and (h) stably transforming a soybean plant with the one or more nucleotide sequences of step (f) or step (g) optimized for expression, thereby producing a stably transformed soybean plant comprising one or more nucleotide sequences optimized for expression in a soybean plant.

Further aspects of the present invention provide transiently transformed soybean plants and stably transformed soybean plants and/or parts thereof made by the methods described herein.

These and other aspects of the invention are set forth in more detail in the description of the invention below.

DETAILED DESCRIPTION

As far as the present inventors are aware there are no binary vector based in planta transient systems available for soybean. This may be due to the difficulty of infiltrating soybean using existing methods such as a needleless syringe, which is commonly used in tobacco and other dicots for infiltration of *Agrobacterium* (See, e.g., Ryu et al. "Agrodrench: a novel and efficient agroinoculation method for virus induced gene silencing in plant roots and various Solanaceae species." *Plant Biology* 2004: Friday, Jul. 24-Wednesday Jul. 28, 2004. Lake Buena Vista, Fla. USA, American Society of Plant Biologists, abstract #834) and vacuum infiltration. The difficulty of infiltration in the case of soybean may be due in part to the thick cuticle and amount of cuticular wax produced on the soybean leaf as well as the soybean's complicated vein system. Therefore, the methods described herein have been developed to overcome this problem and provide methods and compositions for an in planta transient expression system using binary vectors. There are reports of transient expression in soybean using biolistic methods of transformation with cut tissues such as cotyledon, leaf or callus. However, these systems are not ideal systems for carrying out efficacy studies on nucleotide sequences of interest, have not been reproducible, and are not cost effective.

The present invention provides a binary vector based transient expression system that is advantageous not only because it does not have size limitations commonly associated with viral-based expression systems (thus, nucleotide sequences greater than 25 kb in size can be used in an expression cassette to be evaluated) but also expression cassettes driven by different promoters including those of plant origin, expression of multiple polypeptides, and other coding and non-coding genetic elements can be evaluated in a week or less. The in planta transient expression system of the present invention can be used as a reliable predictive model for the performance of expression cassettes in terms of protein production, i.e, low, medium or high level production, in stable transgenic plants. By testing various constructs, one can quickly eliminate (within 2 weeks) under performing construct (i.e, undetectable expression level due to either extremely low expression or other issues related to an underperforming construct). Thus, this allows better expression cassette/construct design, saving significant time and other resources. Importantly, the infiltrated intact plants/parts thereof of the present invention can be used in efficacy studies for nucleotide sequences of interest (s) such as in an insect/disease bioassay.

Accordingly, one aspect of the present invention provides a method of transiently expressing a nucleotide sequence in one or more cells of a soybean plant, comprising: a) abrading the surface of a soybean plant and/or intact part thereof, (i.e., wherein the intact part of the soybean plant is attached to the soybean plant); b) immersing the abraded soybean plant and/or abraded intact part thereof in a solution comprising bacterial cells competent for nucleic acid transfer (e.g., *Agrobacterium, Rhizobium, Sinorhizobium, Mesorhizobium*, etc.) and a surfactant, wherein the bacterial cells comprise the nucleotide sequence to be transiently expressed; c) applying a vacuum (i.e., negative pressure) to the immersed soybean plant and/or intact part thereof of step (b); and d) releasing the vacuum, thereby introducing the solution into the soybean plant and/or intact part thereof, whereby the nucleotide sequence is transiently expressed in one or more cells of the soybean plant.

"Introducing" in the context of the inoculation or infection of a plant with a bacterial solution using a vacuum (negative pressure) means delivery or infiltration of the bacterial solution (i.e., infection medium) into the intercellular spaces of the soybean plant and/or intact part thereof, under conditions whereby the bacteria (e.g., *Agrobacterium, Rhizobium, Sinorhizobium, Mesorhizobium*, etc.)) can infect the cells of the soybean plant and/or intact part thereof, thereby delivering the nucleotide sequence into the cells of the soybean plant and or intact part thereof. Further, "introducing" in the context of the inoculation of a plant with a bacterial solution by contacting the plant or intact part thereof with the solution as described herein means delivery of the bacterial solution (i.e., infection medium) to the surface of the soybean plant and/or intact part thereof under conditions whereby the bacteria can enter the intercellular spaces of the soybean plant and/or intact part thereof and infect the cells of the soybean plant or intact part thereof, thereby delivering the nucleotide sequence into the cells of the soybean plant and/or intact part thereof.

"Introducing" or "delivering" in the context of a plant cell, plant part or plant and a nucleic acid molecule means presenting a nucleic acid molecule to the plant, plant part, and/or plant cell in such a manner that the nucleic acid molecule gains access to the interior of a cell. Where more than one nucleic acid molecule is to be introduced or delivered, these nucleic acid molecules can be assembled as part of a single polynucleotide or nucleic acid construct, or as separate polynucleotide or nucleic acid constructs, and can be located on the same and/or different nucleic acid constructs. Accordingly, these polynucleotides can be introduced or delivered into plant cells in a single transformation event, and/or in separate transformation events. Thus, the term "transformation" as used herein refers to the introduction of a heterologous nucleic acid into a cell. Transformation of a cell may be stable or transient.

"Transient transformation" or "transient expression" in the context of a nucleotide sequence means that a nucleotide sequence is introduced or delivered into the cell and does not integrate into the genome of the cell.

By "stably introducing" or "stably introduced" in the context of a nucleic acid introduced into a cell is intended that the introduced nucleic acid is stably incorporated into the genome of the cell, and thus the cell is stably transformed with the nucleic acid.

"Stable transformation" or "stably transformed" as used herein means that a nucleic acid molecule or nucleotide sequence that is introduced into a cell and integrates into the genome of the cell. As such, the integrated nucleic acid molecule or nucleotide sequence is capable of being inherited by the progeny thereof, more particularly, by the progeny of multiple successive generations. The genome as used herein also includes the plastid genome, and therefore includes integration of the nucleic acid molecule or nucleotide sequence into, for example, the chloroplast genome. Stable transformation as used herein can also refer to a nucleic acid molecule or nucleotide sequence that is maintained extrachromosomally, for example, as a minichromosome.

As described above, the soybean plant of the present invention is intact (i.e., whole), and thus, in some embodiments, the present invention provides a method of assaying the transient expression of a heterologous nucleotide sequence in a soybean plant and/or intact part thereof. Accordingly, in some embodiments of the present invention, one or more intact parts of the soybean plant can be treated (e.g., abraded, immersed, etc) as a separate part (e.g., individually) while remaining attached to plant throughout the treatment. Thus, for example, a leaf of a soybean plant that is intact (i.e., attached to the soybean plant) can be abraded and vacuum infiltrated while remaining attached to the plant. In a further non-limiting example, more than one intact leaf (or any other part) on a soybean plant can be abraded and the more than one leaf (or other part) that was abraded and or the entire intact soybean plant (abraded and unabraded parts) can then be immersed in the infection medium and vacuum infiltrated. It is noted that because the soybean plants of the present invention are intact, they continue to grow following the treatments for transient transformation described herein.

As used herein, an intact part of a soybean plant includes but is not limited to an embryo, pollen, an ovule, a meristematic region, an axillary bud, a seed, a leaf, a leaflet, a cotyledon, a petiole, a stem, a flower, a branch, a fruit, a pod, a root, a root tip, an anther, and the like, that are attached to the soybean plant.

Thus, intact parts of the soybean plant can be abraded in any combination (e.g., one or more leaves, upper and/or lower surface of the leaves (abaxial and/or adaxial), in any combination; one or more leaves in any combination with other intact parts of the soybean plant such as stems, flowers, etc.).

The soybean plant and/or intact part thereof can be of any age. Thus, in some embodiments of the invention, the soybean plant or intact part thereof intact can be about 3 days old (i.e., days after germination) to about 90 days old. In some embodiments, the soybean plant or intact part thereof can be about 5 days old to about 90 days old. In other embodiments, the soybean plant and/or intact part thereof can be about 3 days old to about 30 days old. In still other embodiments, the soybean plant and/or intact part thereof can be about 5 days old to about 30 days old. In further embodiments, the soybean plant and/or intact part thereof can be about 3 days old to about 15 days old. In still further embodiments, the soybean plant or intact part thereof can be about 5 days old to about 15 days old. In additional embodiments, the soybean plant and/or intact part thereof can be about 7 days old to about 14 days old.

In other embodiments of the present invention, the soybean plant and/or intact part thereof is about 1 day old (i.e., days after germination), about 2 days old, about 3 days old, about 4 days old, about 5 days old, about 6 days old, about 7 days old, about 8 days old, about 9 days old, about 10 days old, about 11 days old, about 12 days old, about 13 days old, about 14 days old, about 15 days old, about 16 days old, about 17 days old, about 18 days old, about 19 days old, about 20 days old, about 21 days old, about 22 days old, about 23 days old, about 24 days old, about 25 days old, about 26 days old, about 27 days old, about 28 days old, about 29 days old, about 30 days old, about 31 days old, about 32 days old, about 33 days old, about 34 days old, about 35 days old, about 36 days old, about 37 days old, about 38 days old, about 39 days old, about 40 days old, about 41 days old, about 42 days old, about 43 days old, about 43 days old, about 44 days old, about 45 days old, about 46 days old, about 47 days old, about 48 days old, about 49 days old, about 50 days old, about 51 days old, about 52 days old, about 53 days old, about 54 days old, about 55 days old, about 60 days old, about 65 days old, about 70 days old, about 75 days old, about 80 days old, about 85 days old, about 90 days old, and the like.

The surface of any plant part of the soybean plant can be abraded using any abrasive material (i.e., abrasive) including but not limited to emery, garnet, silicon carbide (SiC, carborundum), aluminum oxide (e.g., sandpaper), diamond and/or quartz, sand, scrubbing pads, wire brush, and the like, and any combination thereof. In some embodiments of the present invention, abrading comprises contacting the intact soybean plant, and/or part thereof, with aluminum oxide sandpaper. The aluminum oxide sandpaper can be of different grit sizes (e.g., fine, medium, coarse grit). Non-limiting standard grit sizes are provided in Table 1.

TABLE 1

CAMI (Coated Abrasive Manufacturers Institute) grit designation and average size particle for different grit types.

| | CAMI grit designation | Average particle size (μm) |
|---|---|---|
| Macrogrits | | |
| Coarse | 40-50 | 336-425 |
| Medium | 60-80 | 265-190 |
| Fine | 100-120 | 140-115 |
| Very fine | 150-220 | 100-68 |
| Microgrits | | |
| Very fine | 240 | 58.5-40.5 |
| Extra fine | 320-360 | 36.0-25.8 |
| Super fine | 400-600 | 23.0-15.3 |
| Ultrafine | 800-1000 | 12.6-8.4 |

In some embodiments of the invention, the surface of the plant part(s) can be abraded using sandpaper having a CAMI grit designation of between about 100 to about 220 and a particle size of about 140 μm to 68 μm. In further embodiments, the surface of the plant part can be abraded using sandpaper having a CAMI grit designation of about 150 and a particle size of about 92 μm. Typically, gently pressing or rubbing the abrasive (e.g., sandpaper) against the surface of the plant part is sufficient to abrade the plant surface. Alternatively, the surface of the plant part can be pressed against the abrasive. In further embodiments of the present invention, the surface of the plant part(s) can be abraded using a laser. In still further embodiments of the invention, the surface of the plant part(s) can be abraded by spraying the plant part(s) with a solution that can abrade. Thus, a solution comprising, for example, sand, emery, garnet, silicon carbide (SiC, carborundum), aluminum oxide (e.g., sandpaper), diamond and/or quartz, tungsten/gold particles, nanoparticles, tungsten (W) nanoparticles, nanodots or nanopowder, and the like, can be sprayed at the surface of the plant part(s), thereby abrading the plant surface. In still further embodiments, a liquid (e.g., water, infection medium, and the like) under pressure and sprayed at the plant surface can be used to abrade the plant surface.

In some embodiments of the present invention, when the plant part that is abraded is a leaf or leaves, the abaxial surface of the leaf is abraded. In other embodiments, the adaxial surface of the leaf is abraded. In further embodiments, both sides of a leaf can be abraded.

As used herein, "surface" means the surface of any intact part of the soybean plant including, but not limited to, an embryo, pollen, an ovule, a meristematic region, an axillary bud, a seed, a leaf, a leaflet, a cotyledon, a petiole, a stem, a flower, a branch, a fruit, a pod, a root, a root tip, an anther, and the like, that are attached to the soybean plant.

Once the surface of the soybean plant and/or intact part thereof is abraded, the abraded soybean plant and/or abraded intact part thereof can be immersed into a solution (e.g., infection medium) comprising bacteria competent for nucleic acid transfer (e.g., *Agrobacterium, Rhizobium, Sinorhizobium, Mesorhizobium*, etc.). The solution or infection medium can be any medium known in the art for use in bacterial infection of plants. As previously described herein, the abraded soybean plant and/or abraded part thereof of the present invention remains intact and viable and continues to grow before, during and after the abrasion treatment and other treatments described herein.

As used herein, "immerse," "immersed," "immersion," "immersing," and grammatical variations thereof, refer to completely covering (submerging) the soybean plant and/or intact part thereof that is to be infiltrated with the infection medium comprising the transformed bacterium (e.g., *Agrobacterium, Rhizobium, Sinorhizobium, Mesorhizobium*, etc.).

In accordance with the methods of the present invention, a nucleotide sequence of interest is introduced into the cells of a bacterial strain competent for nucleic acid transfer (e.g., an *Agrobacterium* strain, *Rhizobium* strain, *Sinorhizobium* strain, *Mesorhizobium* strain, etc.) via conventional transformation methods, and the bacterial strain is then utilized in the transformation methods of the present invention to introduce the nucleotide sequence of interest into the cells of a soybean plant and/or intact part thereof. Many vectors are available for transformation of bacteria competent for nucleic acid transfer (e.g., *Agrobacterium, Rhizobium, Sinorhizobium, Mesorhizobium*, and the like). These typically carry at least one T-DNA border sequence and include vectors such as pBIN19 (Bevan, *Nucleic Acids Res.* 12:8711-8721 (1984)). For the construction of vectors useful in bacterial transformation, see, for example, U.S. Patent Publication No. 2006/0260011, herein incorporated by reference in its entirety.

Thus, bacterial transformation typically involves the transfer of a binary vector carrying the nucleotide sequence of interest to an appropriate *Agrobacterium* strain or other bacterial strain that is competent for nucleic acid transfer, which may depend on the complement of vir genes carried by the host bacterial strain either on a co-resident Ti plasmid or chromosomally (Uknes et al. (1993) *Plant Cell* 5:159-169). The transfer of the recombinant binary vector to host bacterium can be accomplished by a tri-parental mating procedure using *E. coli* carrying the recombinant binary vector, a helper *E. coli* strain that carries a plasmid and which is able to mobilize the recombinant binary vector to the target host bacterial strain (e.g., *Agrobacterium, Rhizobium, Sinorhizobium, Mesorhizobium*, etc. and the like). Alternatively, the recombinant binary vector can be transferred to target host bacterial strain by DNA transformation (Hofgen and Willmitzer (1988) *Nucleic Acids Res.* 16:9877).

Thus, in some embodiments, a bacterium competent for nucleic acid transfer can be *Agrobacterium*. As used herein, "*Agrobacterium*" means a species, subspecies, or strain of *Agrobacterium* that is able to mobilize and selectively transfer T-DNA into a plant or plant cell thereof Any strain of *Agrobacterium* capable of mobilizing and selectively transferring T-DNA into a plant or plant cell can be used in the present invention. In some embodiments, wild-type strains are used. In other embodiments, "disarmed" derivatives of *Agrobacterium* species, in which the tumor-inducing sequences of the Ti plasmid have been removed, are used. In some embodiments, the *Agrobacterium* is *Agrobacterium tumefaciens*. Examples of suitable *A. tumefaciens* strains include, but are not limited to, e.g., EHA101, as described by Hood et al. (1986) *J. Bacteriol.* 168:1291-1301); LBA4404, as described by Hoekema et al. (1983) *Nature* 303:179-180; C58 (pMP90), as described by Koncz and Schell (1986) *Mol. Gen. Genet.* 204:383-396; EHA 105; AGLI; AGL0; and the like as are known in the art, and any combination thereof. In other embodiments of the invention, *Agrobacterium* can be *Agrobacterium rhizogenes* (i.e., *Rhizobium rhizogenes*). Examples of suitable *Agrobacterium rhizogenes* strains include, but are not limited to, 15834, as described by Birot et al. (*Biochem*, 25: 323-35) and R1000.

In further embodiments, in addition to *Agrobacterium* species and strains, other bacterial species and strains thereof, which are competent for nucleic acid transfer can be used in the methods of the present invention (see, for example those described by CAMBIA (www.cambia.org); see also Broothaerts et al. *Nature* 433:629-633 (2005)). Non-limiting examples of non-*Agrobacterium* bacteria competent for nucleic acid transfer include *Sinorhizobium, Mesorhizobium* and *Rhizobium* (Id.).

Accordingly, in some embodiments of the present invention, a soybean plant and/or intact part thereof can be inoculated by contacting the plant and/or intact part thereof with a solution comprising an *Agrobacterium* strain or other bacterial strain competent for nucleic acid transfer that harbors one or more plasmids in a binary vector comprising one or more nucleotide sequences of interest. Binary vectors are vectors capable of reproduction in both *Escherichia coli* and the host bacterium to be used for nucleic acid transfer to the plant (e.g., *Agrobacterium, Rhizobium Sinorhizobium, Mesorhizobium*, etc.). T-DNA binary vectors comprise T-DNA and vir genes located on separate replicons. Numerous such transformation vectors available for plant transformation are known in to those of ordinary skill in the plant transformation arts, and the nucleotide sequences useful in this invention can be used in conjunction with any of these vectors.

Thus, in some embodiments, an infection medium is a medium that has been prepared from cultured bacteria (e.g., *Agrobacterium, Rhizobium, Sinorhizobium, Mesorhizobium*, etc.). In this manner, cells of the bacterial strain comprising the nucleotide sequence of interest to be transformed into the soybean plant and/or intact part thereof are cultured on or in an appropriate medium supplemented with antibiotics selective for the strain and vector (see, for example, the protocol described in the Experimental section herein below). Those of skill in the art are familiar with procedures for growth of bacteria, for example, *Agrobacterium, Rhizobium, Sinorhizobium, Mesorhizobium*, and the like, and suitable culture conditions. Typically the bacterial culture is inoculated from a glycerol stock or streaked plate and is grown overnight. The bacterial cells are then collected and resuspended in a medium suitable for infection of the soybean plant or intact part thereof. As used herein "infection medium" means a suspension of bacterial cells (e.g., *Agrobacterium* spp. *Rhizobium* spp., *Sinorhizobium* spp., *Mesorhizobium* spp., etc.) to be used for infecting the plant material. For example, in some embodiments, an infection medium can comprise Murashige and Skoog salts with vitamins, 2% sucrose, 500 µM MES (pH 5.6), 10 µM MgSO4, and 400 µM acetosyringone.

In some embodiments, the acetosyringone can be used at a concentration in the range of about 50 µM to about 1000 µM, and any range therein. Thus in some embodiments, the the acetosyringone can be used at a concentration of 50 µM, 100 µM, 200 µM, 300 µM, 400 µM, 500 µM, 600 µM, 700 µM, 800 µM, 900 µM, and/or 1000 µM.

The concentration of bacterial cells comprised in the infection medium that can be used with the present invention can be any concentration of bacteria known by those of skill in the art to be effective in transforming/infecting plants. Therefore, in some embodiments of the present invention, the concentration of bacterial cells used can be in a range from about 0.01 $OD_{600}$ to about 4.0 $OD_{600}$. In other embodiments of the invention, the concentration of bacterial cells used can be in a range from about 0.2 $OD_{600}$ to about 2.0 $OD_{600}$. Thus, the concentration of the bacterial cells in the solution (infection medium) can be an $OD_{600}$ of about 0.01, about 0.02, about 0.03, about 0.04, about 0.05, about 0.06, about 0.07, about 0.08, about 0.09, about 0.10, about 0.15, about 0.20, about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, and the like. In some embodiments of the present invention, the concentration of bacterial cells used in the infection medium is 0.2 $OD_{600}$. In other embodiments, the concentration of bacterial cells used in the infection medium is 0.5 $OD_{600}$. In further embodiments of the present invention, the concentration of bacterial cells used in the infection medium is 1.0 $OD_{600}$. In additional embodiments, the concentration of bacterial cells used in the infection medium of the present invention is 2.0 $OD_{600}$.

In some embodiments of the present invention, the solution or infection medium comprising the bacterial cells competent for nucleic acid transfer (e.g., *Agrobacterium, Rhizobium, Sinorhizobium, Mesorhizobium* etc) further comprises one or more surfactants. A surfactant can assist the binding (i.e., attachment/infiltration) of the bacteria cells in the bacterial solution to the surface of the plant which in turn helps facilitate the entry of the bacterial cells and/or T-DNA into the plant cell Any surfactant that is non-toxic to soybean plants can be used with the present invention. Non-limiting examples of surfactants useful in the present invention include methyl end-capped trisiloxane polyethoxylate (Silwet L-77®), polysorbate 20 (Tween® 20), octyl phenol ethoxylate (Triton® X-100), 2-(3-hydroxypropyl)-heptamethyl-trisiloxane (Sylgard 309®), and the like, and any combination thereof. In some embodiments, the surfactant included in the infection medium is Silwet L77®. In some embodiments, the concentration of surfactant can be about 0.01% to about 1%, and any range therein. Thus, in other embodiments, the concentration of the surfactant can be about 0.01%, about 0.02%, about 0.03%, about 0.04%, about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, and the like.

The soybean plant and/or intact part thereof having one or more abraded surfaces and immersed into an infection medium (comprising bacterial cells competent for nucleic acid transfer (e.g., *Agrobacterium, Rhizobium, Sinorhizobium, Mesorhizobium*, etc.) and a surfactant) is then subjected to (e.g., exposed to; contacted with) a vacuum (i.e., negative pressure). Any method of applying a vacuum to a soybean plant and/or intact part thereof can be used with the present invention. Thus, any apparatus capable of applying a vacuum can be used with the present invention. Thus, for example, a bench top vacuum and/or vacuum desiccator can be used.

The vacuum can be applied for about 30 seconds to about 10 minutes. Thus, the vacuum can be applied for about 30 seconds, about 1.0 minute, about 1.5 minutes, about 2.0 minutes, about 2.5 minutes, about 3.0 minutes, about 3.5 minutes, about 4.0 minutes, about 4.5 minutes, about 5.0 minutes, about 5.5 minutes, about 6.0 minutes, about 6.5 minutes, about 7.0 minutes, about 7.5 minutes, about 8.0 minutes, about 8.5 minutes, about 9.0 minutes, about 9.5 minutes, about 10.0 minutes, and the like. Thus, in some embodiments, the vacuum can be applied for about 30 seconds. In other embodiments, the vacuum can be applied for about 1.0 minute. In further embodiments, the vacuum can be applied for about 2.0 minutes. In still other embodiments, the vacuum can be applied for about 5.0 minutes.

The negative pressure applied during the vacuum treatment can be from about 5 cm Hg to about 100 cm Hg, any range therein. In some embodiments of the invention, the negative pressure that is applied is about 5 cm Hg to about 50 cm Hg. In other embodiments, the negative pressure that is applied is about 5 cm Hg to about 25 cm Hg. In further embodiments, the negative pressure that is applied is about 10 cm Hg to about 25 cm Hg. In additional embodiments of the invention, the negative pressure that is applied is about 25 cm Hg. Thus, the negative pressure applied during the vacuum treatment can be about 5 cm Hg, 10 cm Hg, 15 cm Hg, 20 cm Hg, 25 cm Hg, 30 cm Hg, 35 cm Hg, 40 cm Hg, 45 cm Hg, 50 cm Hg, 55 cm Hg, 60 cm Hg, 65 cm Hg, 70 cm Hg, 75 cm Hg, 80 cm Hg, 85 cm Hg, 90 cm Hg, 95 cm Hg, 100 cm Hg, and the like, or any combination thereof.

Following application of the vacuum, the vacuum is released and the solution (infection medium) comprising the bacterial cells (e.g., *Agrobacterium, Rhizobium, Sinorhizobium, Mesorhizobium*, etc.), which comprise the nucleotide sequence to be expressed in the plant, are introduced or infiltrated into the intercellular spaces of the soybean plant and/or part thereof, whereby the bacteria infect the soybean plant cells within the soybean plant and/or intact part thereof, thereby introducing the nucleotide sequence to be expressed into the cell(s) of the soybean plant and/or intact part thereof where it is transiently expressed.

In some embodiments of the present invention, the application and release of the vacuum is repeated one or more times, thereby repeatedly introducing (infiltrating) the solution comprising the bacterial cells (e.g., *Agrobacterium, Rhizobium, Sinorhizobium, Mesorhizobium*, etc.) into the soybean plant and/or intact part thereof. Thus, the application and release of the vacuum can be repeated one time, two times, three times, four times, five times, six times, seven times, eight times, nine times, ten times, eleven times, twelve times, thirteen times, fourteen times, fifteen times, and the like.

In further embodiments of the invention, cuticular waxes on the surface of the soybean plant and/or intact part thereof are at least partially removed by contacting the surface of the soybean plant and/or intact part thereof with an alcohol prior to abrading the surface of the soybean plant and/or intact part thereof. In some embodiments of the invention, intact part of the plant that is contacted with the alcohol is a leaf or leaves and thus, the cuticular waxes are at least partially removed by contacting the surface of the intact leaf or leaves of the soybean plant with alcohol prior to abrading the surface of the intact leaf or leaves of the soybean plant. Non-limiting examples of alcohols useful with the present invention include ethanol, methanol, propanol, butanol, isopropanol, isobutanol, and the like, or any combination thereof. The terms "contact," "contacted," "contacting," and grammatical variations thereof, as used in reference to the application of ethanol to a plant includes any method by which the soybean plant and/or intact part thereof is exposed to, provided with, or by which alcohol is applied to an intact soybean plant and/or part thereof. Some non-limiting examples of contacting a soybean plant and/or intact part thereof with alcohol include wiping, dabbing, immersing, dipping, spraying, sprinkling, misting, atomizing, soaking, pouring, coating, and the like, and combinations thereof.

In some embodiments, the concentration of alcohol used with the present invention is in a range from about 10% to about 100%. In some embodiments of the present invention, the concentration of alcohol is in a range from about 50% to about 70%. Thus, in some embodiments of the invention, the alcohol can be at a concentration of about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, and the like. In some embodiments, the alcohol can be at a concentration of about 96%, 97%, 98% or 99%. In other embodiments of the invention, the alcohol is ethanol at a concentration of 70%.

The infiltrated soybean plant (and intact parts thereof) is placed under conditions sufficient for growth. These conditions are well known to those of skill in the art. For example, the infiltrated soybean plant can be placed in a growth chamber at 25° C. with a 16/8 day/night cycle and a light intensity of 1900 μ-mol-m-2.s-1. To maintain humidity, the plant and intact part thereof can be placed in a container that can be covered.

The tissue from the soybean plant and/or intact part thereof can be harvested for subsequent analysis for expression of the nucleotide sequence of interest at about 2 days to about 15 days post-infiltration, and any range therein. Thus, in some embodiments of the invention, the tissue from the soybean plant and/or intact part thereof can be harvested for analysis at about 2 days post-infiltration, about 3 days post-infiltration, about 4 days post-infiltration, about 5 days post-infiltration, about 6 days post-infiltration, about 7 days post-infiltration, about 8 days post-infiltration, about 9 days post-infiltration, about 10 days post-infiltration, about 11 days post-infiltration, about 12 days post-infiltration, about 13 days post-infiltration, about 14 days post-infiltration, about 15 days post-infiltration, or any combination thereof.

Methods for analyzing expression of nucleotide sequences are known in the art (See, e.g., J. Sambrook et al., "Molecular Cloning: A Laboratory manual," Cold Spring Harbor Laboratory, Cold Spring Harbor, N.Y. (1989); Silhavy et al., "Experiments with Gene Fusions," Cold Spring Harbor Laboratory, Cold Spring Harbor, N.Y. (1984); and Ausubel et al., "Current Protocols in Molecular Biology," Greene Publishing Assoc. and Wiley-Interscience (1987)). Thus, transient transformation may be detected by, for example, an enzyme-linked immunosorbent assay (ELISA) and/or Western blot, which can detect the presence of a peptide or polypeptide encoded by one or more nucleotide sequences introduced into an organism and/or mRNA transcript analysis of the nucleotide sequence of interest.

In further embodiments, the present invention provides a method of transiently expressing a nucleotide sequence in one or more cells of a soybean plant, comprising: a) abrading the surface of a soybean plant and/or intact part thereof, wherein the intact part of the soybean plant is attached to the soybean plant; and b) contacting the abraded soybean plant and/or abraded intact part thereof with a solution comprising bacterial cells competent for nucleic acid transfer (e.g., *Agrobacterium, Rhizobium, Sinorhizobium, Mesorhizobium*, etc.) and a surfactant, wherein the bacterial cells comprise the nucleotide sequence to be transiently expressed, whereby the nucleotide sequence is transiently expressed in one or more cells of the soybean plant.

The soybean plant and/or intact part thereof and the methods for abrading of the surface of the soybean plant and/or intact part thereof are described herein.

Following the abrading of the surface of the soybean plant and/or intact part thereof, the abraded soybean plant and/or intact part is contacted with a solution comprising bacterial cells competent for nucleic acid transfer, such as for example, an *Agrobacterium* solution, The solution comprising bacterial cells competent for nucleic acid transfer or infection medium can be any medium known in the art for use in bacterial infection of plants as described herein.

In some embodiments of the invention, the solution or infection medium comprising the bacterial cells further comprises a surfactant. Non-limiting examples of surfactants include Silwet L-77®, Tween® 20, Triton® X-100, Sylgard 309®, and the like, and any combination thereof. In some embodiments, the infection medium comprises the surfactant Silwet L-77®.

In some aspects of the invention, the step of contacting the plant and/or intact part thereof with a solution comprising bacterial cells includes any method by which the suspension or infection medium is brought into contact with the soybean plant and/or intact part thereof. Thus, the terms "contact," "contacting," and grammatical variations thereof, include any method by which the soybean plant and/or intact part thereof is exposed to, provided with, or by which the infection medium is applied to the intact soybean plant and/or part thereof. Some non-limiting examples of contacting a soybean plant and/or intact part thereof with a solution or infection medium comprising bacterial cells include immersing, dipping, spraying, sprinkling, misting, atomizing, soaking, pouring, coating, and the like, and combinations thereof. These and other procedures for contacting a soybean plant and/or intact part thereof with a solution or infection medium comprising bacterial cells are well-known to those of skill in the art.

The present invention further encompasses soybean plants and/or intact parts thereof in accordance with the embodiments of this invention. Thus, in some embodiments, the present invention provides transiently transformed soybean plants and/or intact parts thereof that are produced by the methods of the present invention.

Additionally, as discussed above, the in planta transient expression system of this invention can be used as model to predict for the performance of nucleic acid constructs/expression cassettes in a stably transformed plant (e.g., expression of RNAs, protein production, etc). When the performance of multiple nucleotides is to be tested, a single vector/expression cassette/nucleic acid molecule comprising the one or more nucleotides can be used. Single or multiple vectors/expression cassettes/nucleic acid molecules can be used with each comprising one or more nucleotide sequences to be expressed. If a construct fails to meet the performance standards, adjustments can be made (e.g., regulatory sequences can be changed, nucleotide sequence position within the construct can be altered, nucleotides within a sequence can be changed, and the like) and the construct tested again. Thus, the performance of a vector can be tested quickly and for relatively low cost using the in-planta transient system versus the higher costs and greater time investment associated with creating stably transforming plants that must then be regenerated and grown for a time before the performance of the vector can be tested. The one or more nucleotide sequences can include, but are not limited to, nucleotide sequences encoding polypeptides, regulatory RNAs, and the like, regulatory regions including, but not limited to, a promoter, a terminator, an enhancer, an intron, an exon, a genetic marker, and/or a transcription factor. Thus, for example, the soybean transient expression system of the present invention can be used to evaluate various types of RNAi constructs (e.g., siRNA, shRNA) for effectiveness in down regulating a native gene present in the soybean or to evaluate RNAi constructs for their ability to effectively control insect infestation and fungal and viral diseases.

Thus, the methods of the present invention can be used to rapidly optimize the expression of a nucleic acid molecule/expression vector comprising one or more nucleotide sequences in a soybean plant or part thereof. A nucleic acid molecule can be transiently expressed in a soybean plant using the methods of the present invention. The level of expression of the one or more nucleotide sequences of the nucleic acid molecule in the transiently transformed soybean can be measured (using methods of measuring expression as known in the art and described herein). If it is determined that at least one of the one or more nucleotide sequences of the nucleic acid molecule does not have the desired level of expression, the nucleotide sequence or nucleic acid molecule can be modified using techniques known in the art to affect expression of nucleotide sequences and the altered nucleotide sequences can then be expressed in the transient expression system of the present invention to determine if the modifications achieved the desired level of expression. This process can be repeated as many times as needed to achieve a desired level of expression. Once the desired level of expression is achieved as indicated by expression in the transient expression system of the present invention, the nucleotide sequence/nucleic acid molecule can be used to stably transform a soybean plant using methods known in the art for transforming plants. Because transient expression of a nucleotide sequence/nucleic acid molecule using the methods of the present invention is predictive of the level of expression of said nucleotide sequence/nucleic acid molecule in a stably transformed soybean plant, the methods of the present invention provide a rapid, cost effective method for evaluating the performance of a nucleotide sequence/nucleic acid molecule prior to undertaking the substantial time and costs associated with developing a soybean plant stably transformed with said nucleotide sequence/nucleic acid molecule.

Accordingly, in one embodiment, the present invention provides a method of predicting the expression of one or more nucleotide sequences in a stably transformed soybean plant, comprising: transiently expressing the one or more nucleotide sequences in one or more cells of a soybean plant by the methods of the present invention; and determining the level of expression of the one or more nucleotide sequences, wherein the level of expression determined in the transiently transformed soybean plant predicts the level of expression in a soybean plant stably transformed with said one or more nucleotide sequences.

In further embodiments, the present invention provides a method of optimizing the expression of one or more nucleotide sequences in a soybean plant for, comprising: (a) transiently expressing one or more nucleotide sequences in one or more cells of a soybean plant by the methods of the present invention; (b) determining the level of expression of the one or more nucleotide sequences in the one or more cells of the transiently transformed soybean plant of step (a); (c) modifying at least one of the one or more nucleotide sequences to optimize the expression of the one or more nucleotide sequences in a soybean plant; (d) transiently expressing the one or more nucleotide sequences of step (c) in one or more cells of a soybean plant by the methods of the present invention; (e) determining the level of expression of the one or more nucleotide sequences of the transiently transformed soybean plant of step (d); and either, (f) verifying that the level of expression of the one or more nucleotide sequences is optimized; or (g) repeating steps (c) through (e) one or more times and then verifying that the level of expression of the one or more nucleotide sequences is optimized, thereby optimizing the level of expression of the one or more nucleotide sequences in a soybean plant. The nucleic acid molecule sequence(s) optimized for expression of the one or more nucleotide sequences can be used to stably transform soybean plants and/or parts thereof.

In additional embodiments, the present invention provides a method of producing a stably transformed soybean plant comprising one or more nucleotide sequences optimized for expression in a soybean plant, comprising, (a) transiently expressing one or more nucleotide sequences in one or more cells of a soybean plant by the methods of the present invention; (b) determining the level of expression of the one or more nucleotide sequences of the nucleic acid molecule in the one or more cells of the transiently transformed soybean plant of step (a); (c) modifying at least one of the one or more nucleotide sequences to optimize the expression of said one or more nucleotide sequences in a soybean plant; (d) transiently expressing the one or more nucleotide sequences of step (c) in one or more cells of a soybean plant according to the methods of the present invention; (e) determining the level of expression of the one or more nucleotide sequences of the transiently transformed soybean plant of step (d); then either, (f) verifying that the level of expression of the one or more nucleotide sequences is optimized; or (g) repeating steps (c) through (e) one or more times and then verifying that the level of expression of the one or more nucleotide sequences is optimized; and (h) stably transforming a soybean plant with the one or more nucleotide sequences of step (f) or step (g) optimized for expression, thereby producing a stably transformed soybean plant comprising one or more nucleotide sequences optimized for expression in a soybean plant.

The present invention further encompasses soybean plants and/or intact parts thereof in accordance with the embodiments of this invention. Thus, in some embodiments, the present invention provides transiently transformed soybean plants and/or intact parts thereof that are produced by the methods of the present invention. In other embodiments, the present invention provides stably transformed soybean plants and/or parts thereof comprising one or more nucleotide sequences optimized by the methods of the present invention.

DEFINITIONS

As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, plant age, optical density, and the like, is meant to encompass variations of ±20%, ±10%, +5%, ±1%, 0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

"Wild type," or "native" nucleic acid molecule, nucleotide sequence, polypeptide or amino acid sequence refers to a naturally occurring or endogenous nucleic acid molecule, nucleotide sequence, polypeptide or amino acid sequence in its naturally occurring or endogenous form (e.g., comprising the same regulatory factors, in the same order, etc., as found in nature). Thus, a "wild type intron" is an intron that is naturally occurring in or endogenous to the organism and is operably associated with the nucleotide sequence(s) as found in the wild-type organism.

As used herein, "heterologous" refers to a nucleic acid molecule or nucleotide sequence that either originates from another species or is from the same species or organism but is modified from either its original form or the form primarily expressed in the cell. Thus, a nucleic acid molecule or nucleotide sequence derived from an organism or species different from that of the cell into which the nucleic acid molecule or nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., a different copy number, under the control of different regulatory sequences and/or in a different position in the genome than that found in nature.

As used herein, the term "polypeptide" encompasses both peptides and proteins, unless indicated otherwise.

Also as used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, anti-sense RNA, any of which can be single stranded or double stranded. The term "nucleotide sequence" as used herein also includes, for example, miRNA, and siRNA, and the like. The terms "nucleotide sequence" "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the U.S. sequence rules, 37 CFR §§1.821-1.825 and the World Intellectual Property Organization (WIPO) Standard ST.25.

As used herein, "optimized expression" or "optimizing expression" in reference to the expression of a nucleotide sequence and/or nucleic acid molecule refers to modifying a nucleotide sequence so as to achieve a desired level of expression. Thus, optimized expression can be higher or lower as compared to the level of expression of the nucleotide sequence prior to the modifications made to the nucleotide sequence or nucleic acid molecule for the purpose of optimizing expression.

Methods of modifying a nucleotide sequence or nucleic acid molecule for the purpose of optimizing the expression of said nucleotide sequence or nucleic acid molecule in a plant are known in the art. Such methods include selection of codons suited for expression in a particular plant species (e.g., optimized for codon usage in soybean), modifying (e.g, altering, adding or removing) one or more regulatory sequences including, but not limited to, a promoter, an intron, a terminator, an exon, a transcription factor, and the like. Levels of expression can also be modified in an expression cassette/nucleic acid molecule by altering the position of the nucleic acid sequences within the nucleic acid molecule/expression cassette.

As used herein, the term "gene" refers to a nucleic acid molecule capable of being used to produce mRNA, antisense RNA, miRNA, siRNA and the like. Genes may or may not be capable of being used to produce a functional protein. Genes can include both coding and non-coding regions (e.g., introns, regulatory elements, promoters, enhancers, termination sequences and 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

As used herein, the terms "fragment" or "portion" when used in reference to a nucleic acid molecule or nucleotide sequence will be understood to mean a nucleic acid molecule or nucleotide sequence of reduced length relative to a reference nucleic acid molecule or nucleotide sequence and comprising, consisting essentially of and/or consisting of a nucleotide sequence of contiguous nucleotides identical or almost identical (e.g., 80%, 81%, 82%, 83%, 84%, 85%, 86%, 87%, 88%, 89%, 90%, 91%, 92%, 93%, 94%, 95%, 96%, 98%, 99% identical) to the reference nucleic acid or nucleotide sequence. Such a nucleic acid fragment according to the invention may be, where appropriate, included in a larger polynucleotide of which it is a constituent.

The term "fragment," as applied to a polypeptide or an amino acid sequence, will be understood to mean an amino acid sequence of reduced length relative to a reference polypeptide or amino acid sequence and comprising, consisting essentially of, and/or consisting of an amino acid sequence of contiguous amino acids identical or substantially identical to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention. A fragment of a polypeptide or protein can be produced by methods well known and routine in the art, for example, by enzymatic and/or other cleavage of naturally occurring peptides or polypeptides and/or by synthetic protocols that are well known.

A polypeptide fragment can be a biologically active fragment. A "biologically active fragment" or "active fragment" refers to a fragment that retains one or more of the biological activities of the reference polypeptide. Such fragments can be tested for biological activities according to methods described in the art, which are routine methods for testing activities of polypeptides, and/or according to any art-known and routine methods for identifying such activities. The production of and testing to identify biologically active fragments of a polypeptide would be well within the scope of one of ordinary skill in the art and would be routine.

An "isolated" nucleic acid molecule or nucleotide sequence or nucleic acid construct or double stranded RNA molecule of the present invention is generally free of nucleotide sequences that flank the nucleic acid of interest in the genomic DNA of the organism from which the nucleic acid was derived (such as coding sequences present at the 5' or 3' ends). However, the nucleic acid molecule of this invention can include some additional bases or moieties that do not deleteriously affect the basic structural and/or functional characteristics of the nucleic acid.

Thus, an "isolated nucleic acid molecule" or "isolated nucleotide sequence" is a nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) that is independent of other sequences. It also includes a recombinant nucleic acid that is part of a hybrid nucleic acid molecule encoding an additional polypeptide or peptide sequence.

As used herein, an "isolated" polypeptide or polypeptide fragment means a polypeptide or polypeptide fragment separated or substantially free from at least some of the other components of the naturally occurring organism, for example, the cellular components or other polypeptides or nucleic acids commonly found associated with the polypeptide.

Thus, the term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary" mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

As used herein, the terms "transformed" and "transgenic" refer to any plant, plant cell, callus, plant tissue, or plant part that contains all or part of at least one recombinant polynucleotide. A recombinant polynucleotide can be stably integrated into a chromosome or stable extra-chromosomal element, so that it is passed on to successive generations. A recombinant polynucleotide can also be transiently expressed and therefore is not passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "transgene" as used herein, refers to any nucleotide sequence used in the transformation of a plant, animal, or other organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic microorganism, or transgenic animal, is an organism into which a transgene has been delivered or introduced.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids or proteins.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 60%, 70%, 80% or 90% sequence identity. In some embodiments, the two nucleotide sequences can have at least 85%, 90%, 95%, 96%, 97%, 98%, 99% or 100% of sequence identity.

An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.,* 2:482-489, 1981, Smith et al., *Nucleic Acids Res.* 11:2205-2220, 1983).

Useful methods for determining sequence identity are also disclosed in Guide to Huge Computers (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215: 403-410 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As discussed previously, the present invention provides advantageous methods for the analysis of the effect(s) of any nucleotide sequence, having a known or unknown function, on gene expression in an intact soybean plant (e.g., regulatory elements). Thus, the expression or effect on expression of any regulatory element can be analyzed in a soybean plant using the methods as described herein. Non-limiting examples of regulatory elements include promoters, enhancers, introns, targeting sequences, transcriptional regulatory regions, and translational termination regions, insulators, Kozak sequences, 5' or/and 3' UTRs, different polyA sequences (terminators), matrix attachment regions (MARS), double standard RNAs, microRNA, and the like, and any non-coding sequences.

The present invention further provides methods for analyzing large molecular weight (greater than 5 kb) nucleic acid molecules such as large expression cassettes, genes with introns greater than 6 Kb, metabolic pathway engineering, and molecular stacking of multiple traits targeting driven by different promoters and targeting to the same or different organelles.

In some embodiments of the present invention, expression cassettes are utilized for expression of nucleic acid molecules and nucleotide sequences. As used herein, "expression cassette" means a nucleic acid molecule having at least a control or regulatory sequence operably linked to a nucleotide sequence of interest. In this manner, for example, plant promoters in operable association with the nucleotide sequences to be expressed are provided in expression cassettes for expression in a plant, plant part and/or plant cell.

For purposes of the invention, the regulatory regions/elements (e.g., promoters, enhancers, targeting sequences, introns, transcriptional regulatory regions, and translational termination regions) can be native/analogous to the soybean plant and/or the regulatory regions can be native/analogous to the other regulatory regions. Alternatively, the regulatory regions may be heterologous to the soybean plant and/or to each other (i.e., the regulatory regions). Thus, for example, a promoter can be heterologous when it is operably linked to a polynucleotide from a species different from the species from which the polynucleotide was derived. Alternatively, a promoter can also be heterologous to a selected nucleotide sequence if the promoter is from the same/analogous species from which the polynucleotide is derived, but one or both (i.e., promoter and polynucleotide) are substantially modified from their original form and/or genomic locus, or the promoter is not the native promoter for the operably linked polynucleotide.

As used herein, the term "promoter" refers to a region of a nucleotide sequence (e.g., a gene or nucleic acid construct) that incorporates the necessary signals for the efficient expression of a coding sequence operably associated with the promoter. This may include sequences to which an RNA polymerase binds, but is not limited to such sequences and can include regions to which other regulatory proteins bind together with regions involved in the control of protein translation and can also include coding sequences.

In particular aspects, a "promoter" of this invention is a promoter capable of initiating transcription of a nucleotide sequence in a cell of a plant. Such promoters include those that drive expression of a nucleotide sequence constitutively, those that drive expression when induced, and those that drive expression in a tissue- or developmentally-specific manner, as these various types of promoters are known in the art.

Examples of constitutive promoters include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter.

In some embodiments, tissue specific promoters can be used. Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Krid1 et al. (1991) *Seed Sci. Res.* 1:209-219; as well as EP Patent No. 255378).

Additional examples of tissue-specific promoters include, but are not limited to, the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313: 810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612). Particularly useful for seed-specific expression is the pea vicilin promoter (Czako et al. (1992) *Mol. Gen. Genet.* 235:33-40; as well as U.S. Pat. No. 5,625,136).

Other useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the present invention include but are not limited to the S-E9 small subunit RuBP carboxylase promoter and the Kunitz trypsin inhibitor gene promoter (Kti3).

In some instances, inducible promoters can be used. Examples of inducible promoters include, but are not limited to, tetracycline repressor system promoters, Lac repressor system promoters, copper-inducible system promoters, salicylate-inducible system promoters (e.g., the PR1 a system), glucocorticoid-inducible promoters (Aoyama et al. (1997) *Plant J.* 11:605-612), and ecdysone-inducible system promoters. Other inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108.

In addition to the promoters described above, an expression cassette also can include other regulatory sequences. As used herein, the term "regulatory sequence" means a nucleotide sequence located upstream (5' non-coding sequences), within or downstream (3' non-coding sequences) of a coding sequence, and which influence the transcription, RNA processing or stability, and/or translation of the associated coding sequence. Regulatory sequences include, but are not limited to, enhancers, translation leader sequences, polyadenylation signal sequences, introns and the like. Thus, for example, an expression cassette of the present invention can comprise three components: a promoter sequence, a coding sequence (cDNA/open reading frame) and a 3' polyadenylation sequence. In some embodiments of the present invention, the expression cassette can include translational and/or transcriptional enhancers or any combination thereof. In other embodiments of the present invention, the expression cassette can include two or more translational enhancers and/or two or more transcriptional enhancers, or any combination thereof. The expression cassettes also can include Kozak sequence, N-terminal targeting sequences including chloroplast transit peptide and signal peptide. Non-limiting examples of introns useful with the present invention include introns of the maize Adh1 gene and Intron 1, which have been shown to enhance gene expression. See, e.g., Callis et al. (1987) *Genes Develop.* 1:1183-1200.

A number of non-translated leader sequences derived from viruses also are known to enhance gene expression and analysis of the effect of these leader sequences on the expression of a selected nucleotide sequence can be done using the methods of the present invention. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' noncoding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

The expression cassette also can optionally include a transcriptional and/or translational termination region (i.e., termination region) that is functional in plants. A variety of transcriptional terminators are available for use in expression cassettes and are responsible for the termination of transcription beyond the transgene and correct mRNA polyadenylation. The termination region may be native to the transcriptional initiation region, may be native to the operably linked nucleotide sequence of interest, may be native to the plant, and/or may be derived from another source (i.e., foreign or heterologous to the promoter, the nucleotide sequence of interest, the plant to be transformed, or any combination thereof). Appropriate transcriptional terminators include, but are not limited to, the CAMV 35S terminator, the tml terminator, the nopaline synthase terminator and the pea rbcs E9 terminator. These can be used in both monocotyledons and dicotyledons, including soybean. In addition, a coding sequence's native transcription terminator can be used.

Regardless of the type of regulatory sequence(s) used, they can be operably linked to a nucleotide sequence of interest to be expressed. As used herein, "operably linked" means that elements of a nucleic acid construct such as an expression cassette are configured so as to perform their usual function. Thus, regulatory or control sequences (e.g., promoters) operably linked to a nucleotide sequence of interest are capable of effecting expression of the nucleotide sequence of interest. The control sequences need not be contiguous with the nucleotide sequence of interest, so long as they function to direct the expression thereof. Thus, for example, intervening untranslated, yet transcribed, sequences can be present between a promoter and a coding sequence, and the promoter sequence can still be considered "operably linked" to the coding sequence. A nucleotide sequence of interest can be operably linked to a regulatory sequence, thereby allowing its expression in a cell and/or subject. In further embodiments of the present invention, a signal sequence can be operably linked to a nucleic acid molecule and or a nucleotide sequence of interest to direct the nucleic acid molecule and/or the nucleotide sequence into a particular cellular compartment.

An expression cassette also can include a nucleotide sequence for a selectable marker, which can be used to select a transformed plant, plant part and/or plant cell. As used herein, "selectable marker" means a nucleic acid molecule that when expressed imparts a distinct phenotype to a plant, plant part and/or plant cell expressing the marker sequence and thus allows such a transformed plant, plant part and/or plant cell to be distinguished from those that do not have the marker (e.g., a soybean plant or intact part thereof that is not transformed). Such a nucleic acid molecule may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Many examples of suitable selectable markers are known in the art and can be used in the expression cassettes described herein. Examples of selectable markers include, but are not limited to, a nucleic acid encoding neo or nptII, which confers resistance to kanamycin, G418, and the like (Potrykus et al. (1985) *Mol. Gen. Genet.* 199:183-188); a nucleic acid encoding bar, which confers resistance to phosphinothricin; a nucleic acid encoding an altered 5-enolpyruvylshikimate-3-phosphate (EPSP) synthase, which confers resistance to glyphosate (Hinchee et al. (1988) *Biotech.* 6:915-922); a nucleic acid encoding a nitrilase such as bxn from *Klebsiella ozaenae* that confers resistance to bromoxynil (Stalker et al. (1988) *Science* 242:419-423); a nucleic acid encoding an altered acetolactate synthase (ALS) that confers resistance to imidazolinone, sulfonylurea or other ALS-inhibiting chemicals (EP Patent Publication No. 154204); a nucleic acid encoding a methotrexate-resistant dihydrofolate reductase (DHFR) (Thillet et al. (1988) *J. Biol. Chem.* 263:12500-12508); a nucleic acid encoding a dalapon dehalogenase that confers resistance to dalapon; a nucleic acid encoding a mannose-6-phosphate isomerase (also referred to as phosphomannose isomerase (PMI)) that confers an ability to metabolize mannose (U.S. Pat. Nos. 5,767,378 and 5,994,629); a nucleic acid encoding an altered anthranilate synthase that confers resistance to 5-methyl tryptophan; and/or a nucleic acid encoding hph that confers resistance to hygromycin. One of skill in the art is capable of choosing a suitable selectable marker for use in an expression cassette of this invention.

Additional selectable markers include, but are not limited to, a nucleic acid encoding β-glucuronidase or uidA (GUS) that encodes an enzyme for which various chromogenic substrates are known; an R-locus nucleic acid that encodes a product that regulates the production of anthocyanin pigments (red color) in plant tissues (Dellaporta et al., "Molecular cloning of the maize R-nj allele by transposon-tagging with Ac" pp. 263-282 In: *Chromosome Structure and Function: Impact of New Concepts,* 18th Stadler Genetics Symposium (Gustafson & Appels eds., Plenum Press 1988)); a nucleic acid encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleic acid encoding xylE that encodes a catechol dioxygenase (Zukowsky et al. (1983)

Proc. Natl. Acad. Sci. USA 80:1101-1105); a nucleic acid encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleic acid encoding β-galactosidase, an enzyme for which there are chromogenic substrates; a nucleic acid encoding luciferase (lux) that allows for bioluminescence detection (Ow et al. (1986) *Science* 234:856-859); a nucleic acid encoding aequorin which may be employed in calcium-sensitive bioluminescence detection (Prasher et al. (1985) *Biochem. Biophys. Res. Comm.* 126:1259-1268); or a nucleic acid encoding green fluorescent protein (Niedz et al. (1995) *Plant Cell Reports* 14:403-406). One of skill in the art is capable of choosing a suitable selectable marker for use in an expression cassette of this invention.

An expression cassette also can include a coding sequence for one or more polypeptides for agronomic traits that primarily are of benefit to a seed company, grower or grain processor, for example, bacterial pathogen resistance, fungal resistance, herbicide resistance, insect resistance, nematode resistance and/or virus resistance. See, e.g., U.S. Pat. Nos. 5,304,730; 5,495,071; 5,569,823; 6,329,504 and 6,337,431. The trait also can be one that increases plant vigor or yield (including traits that allow a plant to grow at different temperatures, soil conditions and levels of sunlight and precipitation), or one that allows identification of a plant exhibiting a trait of interest (e.g., a selectable marker, etc.). Various traits of interest, as well as methods for introducing these traits into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903, 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/. Thus, in some embodiments, present invention provides a rapid method for analysis of the expression of nucleotide sequences which encode polypeptides that confer important agronomic traits in soybean or encode regulatory elements that affect important agronomic traits in soybean.

Accordingly, a polypeptide useful with the present invention (e.g., a heterologous polypeptide) can be any polypeptide. Non-limiting examples of such polypeptides include those resulting in agronomically important traits such as herbicide resistance, virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431. The polypeptide may also be one that results in an increase in plant vigor and/or yield (including polypeptides that allow a plant to grow at different temperatures, soil conditions and levels of sunlight and precipitation), and/or one that allows identification of a plant exhibiting a trait of interest (e.g., selectable marker gene, etc.).

In some embodiments of the present invention, nucleic acid molecules conferring resistance (sometimes referred to as tolerance) to an herbicide that inhibits the growing point or meristem, such as an imidazalinone or a sulfonylurea can be suitable. Exemplary nucleic acids in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleic acids conferring resistance to glyphosate are also suitable. See, e.g., U.S. Pat. No. 4,940,835 and U.S. Pat. No. 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Nucleotide sequences encoding resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Nucleotide sequences encoding resistance to herbicides that inhibit photosynthesis are also useful with the invention. Herbicides that inhibit photosynthesis include but are not limited to triazine and a benzonitrile (nitrilase). See, U.S. Pat. No. 4,810,648. Nucleotide sequences encoding resistance to 2,2-dichloropropionic acid, sethoxydim, haloxyfop, imidazolinone herbicides, sulfonylurea herbicides, triazolopyrimidine herbicides, s-triazine herbicides and bromoxynil are also useful. Also suitable are nucleotide sequences that confer resistance to a protox enzyme, or provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Nucleotide sequences useful for conferring insect or pest resistance include, for example, those that encode toxins identified in Bacillus organisms. Nucleic acids encoding *Bacillus thuringiensis* (Bt) toxins from several subspecies have been cloned and recombinant clones have been found to be toxic to lepidopteran, dipteran and coleopteran insect larvae (for example, various delta-endotoxin genes such as Cry1Aa, Cry1Ab, Cry1Ac, Cry1B, Cry1C, Cry1D, Cry1Ea, Cry1Fa, Cry3A, Cry9A, Cry9C and Cry9B; as well as genes encoding vegetative insecticidal proteins such as Vip1, Vip2 and Vip3). A full list of Bt toxins can be found on the world-wide web at *Bacillus thuringiensis* Toxin Nomenclature Database maintained by the University of Sussex (see also, Crickmore et al. (1998) *Microbiol. Mol. Biol. Rev.* 62:807-813).

Polypeptides that are suitable for production in plants further include those that improve or otherwise facilitate the conversion of harvested cane into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content and/or increased vitamin content. Polypeptides of the invention also include, for example, those resulting in or contributing to a reduced content of an unwanted component in a harvested crop, e.g., phytic acid, or sugar degrading enzymes. By "resulting in" or "contributing to" is intended that the polypeptide of the invention can directly or indirectly contribute to the existence of a trait of interest (e.g., increasing cellulose degradation by the use of a heterologous cellulase enzyme).

In some embodiments of the invention, the polypeptide can contribute to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced using xylanases. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in T reesei (Tenkanen et al. (1992) *Enzyme Microb. Technol*, 14:566; Torronen et al. (1992) *Bio/Technology* 10:1461; and Xu et al. (1998) *Appl. Microbiol. Biotechnol.* 49:718).

In another embodiment, the polypeptide of the invention can be a polysaccharide degrading enzyme. Plants producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; and g) other enzymes such as α-L-fucosidase (EC 3.2.1.51), α-L-rhamnosidase (EC 3.2.1.40), levanase (EC 3.2.1.65), inulanase (EC 3.2.1.7), and the like.

Further enzymes which may be used include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes (polypeptides of this invention) include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

Thus, by introducing nucleotide sequences encoding polypeptides of interest such as those discussed above, the present invention provides a rapid means of analyzing the effects of their production on an intact soybean plant. Thus, for example, whole, intact plants that are transiently transformed using the methods of the present invention can be used to test for herbicide resistance/tolerance, insect resistance/tolerance, fungal and bacterial resistance/tolerance, and the like. In other embodiments, a whole intact plant that is transiently transformed using the methods of the present invention can be used to investigate enzyme expression and digestibility.

In some embodiments, a polypeptide of the invention further can comprise a leader peptide. Thus, the methods of the present invention can be used to analyze of the effect of a leader peptide on the production of a polypeptide. As is well known in the art, a leader peptide is a peptide that is encoded upstream (5' end of the coding sequence) of a larger open reading frame. Any leader peptide can be used with the methods of the present invention. A leader peptide can be a peptide that is found in nature or it can be a synthetic peptide designed to function as a leader peptide.

Non-limiting examples of leader peptides include signal peptides, transit peptides, targeting peptides, signal sequences, and the like. As is well known in the art, signal/transit peptides target or transport a protein encoded by a nuclear gene to a particular organelle such as the mitochondrion, plastids (e.g., apicoplast, chromoplast, chloroplast, cyanelle, thylakoid, amyloplast, and the like),and/or microbodies (e.g., single membrane-bounded small organelles, such as peroxisomes, hydrogenosomes, glyoxysomes and/or glycosome).

Further, leader peptides are well known in the art and can be found in public databases such as the "Signal Peptide Website: An Information Platform for Signal Sequences and Signal Peptides." (www.signalpeptide.de); the "Signal Peptide Database" (proline.bic.nus.edu.sg/spdb/index.html) (Choo et al., *BMC Bioinformatics* 6:249 (2005)(available on www.biomedcentral.com/1471-2105/6/249/abstract); ChloroP (www.cbs.dtu.dk/services/ChloroP/; predicts the presence of chloroplast transit peptides (cTP) in protein sequences and the location of potential cTP cleavage sites); LipoP (www.cbs.dtu.dk/services/LipoP/; predicts lipoproteins and signal peptides in Gram negative bacteria); MITOPROT (ihg2.helmholtz-muenchen.de/ihg/mitoprot.html; predicts mitochondrial targeting sequences); PlasMit (gecco-.org.chemie.uni-frankfurt.de/plasmit/index.html; predicts mitochondrial transit peptides in *Plasmodium falciparum*); Predotar (urgi.versailles.inra.fr/predotar/predotar.html; predicts mitochondrial and plastid targeting sequences); PTS1 (mendel.imp.ac.at/mendeljsp/sat/pts1/PTS1predictor.jsp; predicts peroxisomal targeting signal 1 containing proteins); SignalP (www.cbs.dtu.dk/services/SignalP/; predicts the presence and location of signal peptide cleavage sites in amino acid sequences from different organisms: Gram-positive prokaryotes, Gram-negative prokaryotes, and eukaryotes. The SignalP method incorporates a prediction of cleavage sites and a signal peptide/non-signal peptide prediction based on a combination of several artificial neural networks and hidden Markov models; and TargetP (www.cbs.dtu.dk/services/TargetP/); predicts the subcellular location of eukaryotic proteins—the location assignment is based on the predicted presence of any of the N-terminal presequences: chloroplast transit peptide (cTP), mitochondrial targeting peptide (mTP) or secretory pathway signal peptide (SP)). (See also, von Heijne, G., *Eur J Biochem* 133 (1) 17-21 (1983); Martoglio et al. *Trends Cell Biol* 8 (10):410-5 (1998); Hegde et al. *Trends Biochem Sci* 31(10):563-71 (2006); Dultz et al. *J Biol Chem* 283(15):9966-76 (2008); Emanuelsson et al. *Nature Protocols* 2(4) 953-971(2007); Zuegge et al. 280 (1-2);19-26 (2001); Neuberger et al. *J Mol Biol.* 328(3):567-79 (2003); and Neuberger et al. J Mol Biol. 328(3):581-92 (2003)).

The present invention will now be described with reference to the following examples. These examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Construction of Vectors and *Agrobacterium* transformation

Standard recombinant DNA and molecular cloning techniques used here are well known in the art and are described by Sambrook et al., "Molecular Cloning: A Laboratory Manual," Cold Spring Harbor Laboratory, Cold Spring Harbor, N.Y. (1989), Silhavy et al., "Experiments with Gene Fusions," Cold Spring Harbor Laboratory, Cold Spring Harbor, N.Y. (1984) and Ausubel et al., "Current Protocols in Molecular Biology," Greene Publishing Assoc. and Wiley-Interscience (1987). Specifically, construct 17282 containing the nucleotide sequence encoding the gus protein (beta glucuronidase), was transferred into *Agrobacterium tumefaciens* strains LBA4404 containing helper plasmid (pSB1) using standard methods.

Preparation of *Agrobacterium* cultures was carried out as described by Azhakanandam et al., *Plant Mol. Biol.* 63: 393-404 (2007). In brief, the genetically modified agrobacteria were grown overnight in 50 mL of YP medium containing 100 µM acetosyringone and 10 µM MES (pH 5.6), and then pelleted by centrifugation at 4000×g for 10 min. The pellets were resuspended in infection medium [Murashige and Skoog salts with vitamins, 2% sucrose, 500 µM MES (pH 5.6), 10 µM MgSO4, and 400 µM acetosyringone] to $OD_{600}$=0.5 or 1.0 and subsequently held at 28 degrees C. for 2-3 hours.

Example 2

Soybean Seedlings for Agroinfection (Before and After Treatment)

In-planta transient expression systems were developed using intact young soybean seedlings (6-21 days old). The following procedures were used for each of the Examples below. Seeds were germinated under greenhouse conditions in 2.5" pots filled with Fafard germination mix. The seedlings were kept under a 14/10 day/night cycle with a day light intensity of 2000 µ-mol-m-2.s-1 maintained with supplemental lighting. The temperature was maintained steady between 23° C.-26° C. To facilitate infiltration, the seedlings were watered 1-2 hours prior to treatment to keep the leaf turgid and the stomata open. The specific treatments of the seedlings are described below.

Treated plants were transferred to trays and maintained under growth chamber conditions set at 25° C. with a 16/8 day/night cycle and a light intensity of 1900 µ-mol-m-2.s-1. The plants were covered to maintain humidity.

Leaf tissue was harvested about 3-5 days post infiltration for subsequent analysis. Approximately 20-30 mg of leaf tissue was extracted with 0.5 ml BB/PVP/Tw extraction buffer (0.1M borate, pH 7.5 containing 0.5% Tween-20 and 0.2% polyvinyl pyrrolidone). Supernatants were assayed and total soluble protein was determined by the BCA method (Pierce BCA Protein assay kit, Cat #23223 and 23224) using ovalbumin as a standard.

Example 3

Quantitative ELISA

High-binding 96-well plates (Nunc Maxisorp) were coated at 4° C. overnight with 2 µg/ml rabbit anti-GUS IgG (Sigma G5545) in 25 mM borate, 75 mM NaCl, pH 8.5 (100 µl/well). Plates were washed three times with 10 mM Tris, pH 8.0 containing 0.05% Tween-20 and 0.2% NaN3. Samples or standards (GUS Type VII-A, Sigma G7646) were added to the plate (100 µl/well), incubated for 1 hr at room temperature with shaking, and washed five times. 100 µt/well of 2 µg/ml HRP-labeled rabbit anti-GUS IgG (Invitrogen A5790 conjugated to HRP) was then added to the plate, incubated for 1 hr at room temperature with shaking, and washed as before. The HRP-conjugated antibody was detected by adding 100 µl/well tetramethylbenzidine (TMB, Sigma T0440) and developing for 30 min at room temperature. The reaction was stopped by the addition of 100 µl/well of 0.1N HCl. The absorbance was measured at 450 nm with 620 as a reference using a microplate reader (Tecan Sunrise, Research Triangle Park, N.C.). The GUS standard curve uses a 4-parameter curve fit. The curve is plotted linear vs. log with a range from 0 to 320 ng/ml.

Example 4

Vacuum Assisted Infiltration of Soybean

For each of the treatments in Example 4, *Agrobacterium* strain LBA4404 (pSB1) containing 17282 construct with GUS was used. The concentration of the bacterial cells in the infection medium was $OD_{600}$ of about 1.0. Four plants (16 days post germination) were used per treatment and six samples per plant (collected from two trifoliate leaves) were analyzed. For ELISA analysis (see Example 3), the samples were harvested 4 day post infiltration.

Treatment 1: Vacuum Infiltration Only.

The plants were immersed into a solution (infection medium) comprising *Agrobacterium* cells (prepared as described in Example 1) and a vacuum was applied. The infection medium included Murashige and Skoog salts with vitamins, 2% sucrose, 500 µM MES (pH 5.6), 10 µM MgSO4, and 400 µM acetosyringone. A bench top vacuum was used and the vacuum was applied at 25 cm Hg for about 1-2 minutes. Upon release of the vacuum, the *Agrobacterium* solution entered the intercellular spaces of the leaves.

Treatment 2: Ethanol and Vacuum Infiltration.

A paper towel wetted with 70% ethanol was used to wipe the bottom side of the leaves (abaxial surface of the leaf) to remove waxy material. Following removal of the cuticular waxes with the ethanol, the treated plants were immersed into a solution (or infection medium) comprising *Agrobacterium* and a vacuum was applied as described above in Treatment 1. Upon release of the vacuum, the *Agrobacterium* solution entered the intercellular spaces of the leaves.

Treatment 3: Surfactant and Vacuum Infiltration.

A non-ionic surfactant, Silwet L-77®, at a concentration of 0.04%, was included in the *Agrobacterium* suspension culture (infection medium) used for infection (described above in Treatment 1). Thus, the plants were immersed into the infection medium comprising the surfactant and a vacuum was applied as described above in Treatment 1. Upon release of the vacuum, the *Agrobacterium* solution entered the intercellular spaces of the leaves.

Treatment 4: Sandpaper and Vacuum Infiltration:

3M aluminum oxide sandpaper (extra fine) was pressed against the abaxial side of the whole leaf to make a gentle abrasion on the leaf surface prior to application of a vacuum. The abraded leaves were immersed into a solution (or infection medium) comprising *Agrobacterium* and a vacuum was applied as described above in Treatment 1. Upon release of the vacuum, the *Agrobacterium* solution entered the intercellular spaces of the leaves.

Treatment 5: 70% Ethanol, Sandpaper, Surfactant, and Vacuum Infiltration.

A paper towel wetted with 70% ethanol was used to wipe the bottom side of the leaves (abaxial surface of the leaf) to remove waxy material. Following removal of the cuticular waxes with the ethanol, the leaves were then abraded with sandpaper as described above in Treatment 4. The alcohol/sandpaper treated plants were immersed into a solution (or infection medium) comprising *Agrobacterium* and a non-ionic surfactant, Silwet L77®, at a concentration of 0.04% (as described in Treatment 3 above). A vacuum was applied as described above in Treatment 1. Upon release of the vacuum, the *Agrobacterium* solution entered the intercellular spaces of the leaves.

Treatment 6: Sandpaper, Surfactant, and Vacuum Infiltration.

3M aluminum oxide sandpaper (extra fine) was pressed against the abaxial side of the whole leaf to make a gentle abrasion on the leaf surface prior to application of a vacuum. The abraded leaves were immersed into a solution (or infection medium) comprising *Agrobacterium* and a non-ionic surfactant, Silwet L-77®, at a concentration of 0.04%. A vacuum was applied as described above in Treatment 1. Upon release of the vacuum, the *Agrobacterium* solution entered the intercellular spaces of the leaves.

Treatment 7: 70% Ethanol, Sandpaper, and Vacuum Infiltration.

A paper towel wetted with 70% ethanol was used to wipe the bottom side of the leaves (abaxial surface of the leaf) to remove waxy material. Following removal of the cuticular waxes with the ethanol, the leaves were then abraded with sandpaper as described above in Treatment 4. The alcohol/sandpaper treated plants were immersed into a solution (or infection medium) comprising *Agrobacterium* and a vacuum was applied as described above in Treatment 1. Upon release of the vacuum the *Agrobacterium* solution entered the intercellular spaces of the leaves.

Treatment 8: 70% Ethanol, Surfactant, and Vacuum Infiltration.

A paper towel wetted with 70% ethanol was used to wipe the bottom side of the leaves (abaxial surface of the leaf) to remove waxy material. Following removal of the cuticular waxes with the ethanol, the alcohol treated plants were immersed into a solution (or infection medium) comprising *Agrobacterium* and a non-ionic surfactant, Silwet L77®, at a concentration of 0.04%. The infection medium comprising the surfactant is described in Treatment 3, above. A vacuum was applied as described above in Treatment 1. Upon release of the vacuum, the *Agrobacterium* solution entered the intercellular spaces of the leaves.

The data for Treatments 1-8 above is provided in Table 2, below.

TABLE 2

Infiltration of soybean plants with *Agrobacterium* strain containing 17282 (gus) using vacuum alone or with different treatments as described above.

| Genotype | Treatment | GUS marker protein Average* (GUS ng/mg total soluble protein (TSP)) |
|---|---|---|
| var. Jack | 1. Vacuum only | 1.46 |
| | 2. Ethanol and vacuum | 51.08 |
| | 3. Surfactant and vacuum | 72.19 |
| | 4. Sandpaper and vacuum | 219.81 |
| | 5. Ethanol, sandpaper, surfactant and vacuum | 497.16 |
| | 6. Sandpaper, surfactant and vacuum (no ethanol) | 362.09 |
| | 7. Ethanol, sandpaper, and vacuum (no surfactant) | 127.87 |
| | 8. Ethanol, surfactant and vacuum (no sandpaper) | 44.38 |

*Four plants (16 days old) were used per treatment.

TABLE 3

Statistical analysis of the results of the different treatments in Table 2 using the student t-test.

| t-test | P Value (significance level of 0.01) |
|---|---|
| Ethanol, sandpaper, surfactant and vacuum (Treatment. 5) vs sandpaper, surfactant and vacuum (i.e., no ethanol; Treatment 6)) | 0.241428184 |
| Ethanol, sandpaper, surfactant and vacuum (Treatment. 5) vs ethanol, surfactant and vacuum (i.e., no sandpaper; Treatment 8) | 0.000198537029889437** |
| Ethanol, sandpaper, surfactant and vacuum (Treatment. 5) vs surfactant and vacuum (i.e., no sand paper/no ethanol; Treatment 3) | 0.0000300895046502825** |
| Ethanol, sandpaper, surfactant and vacuum (Treatment. 5) vs ethanol, sandpaper, and vacuum (i.e., no surfactant; Treatment 7) | 0.0000736544148373222** |
| Ethanol, sandpaper, surfactant and vacuum(Treatment. 5) vs sandpaper and vacuum (Treatment 4) | 0.00577380673221763** |

TABLE 3-continued

Statistical analysis of the results of the different treatments in Table 2 using the student t-test.

| t-test | P Value (significance level of 0.01) |
|---|---|
| Ethanol, sandpaper, surfactant and vacuum (Treatment 5) vs ethanol and vacuum (Treatment 2) | 0.000020995769469533** |
| Ethanol, sandpaper, surfactant and vacuum (Treatment 5) vs vacuum (Treatment 1) | 2.33196549717962E–08** |

**significantly different

The various treatments used in establishing the in planta soybean transient expression system is summarized in Table 2. The results revealed that using vacuum infiltration alone was ineffective for soybean as little or no GUS expression was obtained in the infiltrated soybean leaves (only one leaf sample out of 24 samples collected from four infiltrated plants was positive for GUS expression). Such a level of expression is not useful for evaluation of expression cassettes or regulatory sequences in soybean. However, the combination of abrasive (sandpaper), surfactant and vacuum infiltration or alcohol (ethanol), abrasive, surfactant and vacuum infiltration provided a surprising improvement in the in planta transient system for soybean. As can be seen from Tables 2 and 3, the expression levels were significantly improved using the methods of the present invention with Treatment 5 (alcohol, sandpaper, surfactant and vacuum infiltration) providing the highest level of GUS expression. Thus, while vacuum infiltration alone was ineffective in establishing an in planta soybean transient expression assay, its combination with an abrasive and surfactant or an alcohol, abrasive and surfactant was surprisingly effective.

Example 5

*Agrobacterium* Infection of Soybean Leaves Without a Vacuum

Sixteen day old soybean plants were pre-treated with alcohol (70% ethanol), abraded with fine sandpaper and immersed (dipped) in an infection medium comprising *Agrobacterium* cell and a surfactant. A paper towel wetted with 70% ethanol was used to wipe the bottom side of the leaves (abaxial surface of the leaf) to remove waxy material. Following removal of the cuticular waxes with the ethanol and prior to application of a vacuum, the abaxial side of the leaf surface was then abraded with 3M aluminum oxide sandpaper (extra fine) by pressing the sandpaper against the whole leaf to make a gentle abrasion on the leaf surface. The ethanol treated/abraded leaves were immersed (dipped) into a solution comprising *Agrobacterium* cells (LBA4404 comprising construct 17282; described above in Example 1) (i.e., infection medium) for 5 minutes at room temperature. The infection medium included Murashige and Skoog salts with vitamins, 2% sucrose, 500 µM MES (pH 5.6), 10 µM MgSO4, and 400 µM acetosyringone. Just before the immersion/dipping of the plants, a surfactant, 0.04% Silwet®, was added to the infection medium.

Treated plants were removed from the solution and transferred to trays and maintained under growth chamber conditions set at 25° C. with a 16/8 day/night cycle and a light intensity of 1900 µ-mol-m-2.s-1. The plants were covered to maintain humidity.

Two negative controls were used. The *Agrobacterium* negative control included treatment of the intact leaves (abaxial side) of the soybean plant with alcohol, abrasion of the surface of the intact leaves and then dipping of the intact plant with treated leaves in infection medium comprising *Agrobacterium* strain LBA4404 (pSB1) without any nucleotide sequence encoding gus. An additional negative control included wild-type soybean plants of the same variety (Jack) without any treatment (uninfiltrated wild-type plants).

Leaf tissue was harvested four days post infiltration for subsequent analysis. Approximately 20-30 mg of leaf tissue was extracted with 0.5 ml BB/PVP/Tw extraction buffer (0.1M borate, pH 7.5 containing 0.5% Tween-20 and 0.2% polyvinyl pyrrolidone). Supernatants were assayed and total soluble protein was determined by the BCA method (Pierce BCA Protein assay kit, Cat #23223 and 23224) using ovalbumin as a standard. The data is presented in Table 4.

TABLE 4

Agroinfection without vacuum infiltration.

| Genotype | Treatment | GUS marker protein Average* (GUS ng/mg TSP) |
|---|---|---|
| Jack | Alcohol, abrasion and dipping in *Agrobacterium* strain LBA4404 (pSB1) + construct 17282 (gus) | 370.19 ± 169.83 |
|  | Alcohol, abrasion and dipping in *Agrobacterium* strain LBA4404 (pSB1) (negative control) | 0 |
|  | Uninfiltrated wild type plants (negative control) | 0 |

*The experiment was repeated two times using 4 plants per experiment.

Soybean plants are difficult to infiltrate and obtain significant expression of nucleotide sequences of interest using binary vectors with any existing methods, such as a syringe without a needle or via vacuum infiltration. However, the methods of the present invention demonstrate a successful and novel approach that provides significant expression of nucleotide sequences of interest in an in planta (intact whole plants) transient expression system using binary vectors without a syringe or vacuum infiltration. These methods provide simple and inexpensive methods for screening, for example, expression cassettes.

Example 6

Rapid Screening for the Efficacy of an Insect Resistance Gene (vip3a) Using an Insect Bioassay To validate the usefulness of the in planta transient expression system described in the present invention, an insect bioassay was performed on five plants infiltrated with *Agro-*

*bacterium* cells comprising a construct (construct A) comprising a nucleotide sequence encoding vip3a. vip3a is an 89-kDa protein secreted by Bacillus thuringiensis during vegetative growth.

Specifically, paper towel wetted with 70% ethanol was used to wipe the bottom side of the leaves (abaxial surface of the leaf) to remove waxy material. Following removal of the cuticular waxes with the ethanol, the alcohol treated plants were immersed into a solution (or infection medium) comprising *Agrobacterium* and a non-ionic surfactant, Silwet L-77®, at a concentration of 0.04%. The infection medium comprising the surfactant is described in Example 4, Treatment 3, above. A vacuum was applied as described above in Example 4, Treatment 1. Upon release of the vacuum, the *Agrobacterium* solution entered the intercellular spaces of the leaves.

Leaf tissue was harvested 4 days post infiltration. The infiltrated leaves were subjected to the insect feeding for 7 days and readings were taken on the 7-8th day. The data is presented in Table 5.

sion system in which no vacuum infiltration is used as described in Example 5, two constructs were used to test the predictive model for expression. Each construct includes a nucleotide sequence encoding an *Avena sativa* (oat) HPPD (4-hydroxyphenylpyruvate dioxygenase). In construct B, the nucleotide sequence is codon optimized for expression in soybean while construct C has a wild type HPPD coding sequence from oat. In addition, both constructs have minimal viral promoters in addition to enhancers. The construct B has one transcriptional enhancer (enhancer region from Figwort mosaic virus (FMV)) and a TMV Omega 5'UTR leader sequence known to enhance expression) and construct C has a dual transcriptional enhancer (FMV+35S (enhancer region from Figwort mosaic virus (FMV), Cauliflower mosaic virus 35S enhancer regions) and also a translational enhancer, TMV Omega 5'UTR leader sequence. The results for the methods using vacuum infiltration are provided in Table 6 and the results for the methods without vacuum infiltration are provided in Table 7.

TABLE 5

Insect bioassay using soybean leaves transiently infected with construct A comprising the nucleotide sequence encoding the vip3a protein.

| | Replicate # 1 | | | | Replicate # 2 | | | |
|---|---|---|---|---|---|---|---|---|
| Sample Name | Living Larvae | Dead Larvae | % Mortality | % Leaf Damage | Living Larvae | Dead Larvae | % Mortality | % Leaf Damage |
| Vector control (negative) | 10 | 0 | 0 | 100 | 9 | 0 | 0 | 100 |
| Infection medium (negative) | 10 | 0 | 0 | 100 | 10 | 0 | 0 | 90 |
| Uninfiltrated (negative) | 10 | 0 | 0 | 40 | 10 | 0 | 0 | 80 |
| construct A (vip3a) | 0 | 10 | 100 | 0 | 0 | 9 | 90 | 0 |
| construct A (vip3a) | 2 | 8 | 80 | 30 | 0 | 10 | 100 | 0 |
| construct A (vip3a) | 0 | 10 | 100 | 2 | 1 | 9 | 90 | 10 |
| construct A (vip3a) | 0 | 10 | 100 | 0 | 0 | 10 | 100 | 0 |
| construct A (vip3a) | 0 | 10 | 100 | 0 | 0 | 9 | 90 | 2 |

The results of this experiment showed that vip3a expression in soybean using the soybean in planta transient expression system as described herein results in 80-100% fall armyworm mortality. The controls (vector control (e.g., *Agrobacterium* containing a binary vector without vip3a), infection medium only (i.e., no *Agrobacterium*) and uninfiltrated wild type soybean plants)) showed little or no mortality (Table 5).

Example 7

The Soybean in Plant Transient Expression System as a Predictive Model for the Expression of Constructs in Stably Transformed Soybean Plants Using the soybean in planta transient expression system involving vacuum infiltration method as described in Treatment 5 (Example 4), or the soybean in planta transient expression

TABLE 6

Comparison of expression of HPPD in the soybean in-planta transient expression system (using vacuum infiltration) versus expression of HPPD in stably transformed soybean plants.

| | Average* HPPD Expression [ng/mg (Total Soluble Protein)] | |
|---|---|---|
| Constructs | Transient | Stable transgenic plants |
| construct B (Codon optimized HPPD) | 2.46 | 260.12 |
| construct C (Non-codon optimized HPPD) | 93.09 | 2396.17 |
| Uninfiltrated wild type plants (negative control) | 0 | 0 |
| Infiltration with infection medium only (negative control) | 0 | 0 |

*The first trifoliate leaves from four plants (16 days old) were used per treatment.

TABLE 7

Comparison of expression of HPPD in the soybean in-planta transient expression system without vaccum infiltration versus expression of HPPD in stably transformed soybean plants.

| Constructs | Average* HPPD Expression [ng/mg (Total Soluble Protein)] | |
| --- | --- | --- |
| | Transient | Stable transgenic plants |
| construct B (Codon optimized HPPD) | 0.78 | 260.12 |
| construct C (Non-codon optimized HPPD) | 26.61 | 2396.17 |
| Uninfiltrated wild type plants (negative control) | 0 | 0 |
| Infiltration with infection medium only (negative control) | 0 | 0 |

*The first trifoliate leaves from four plants (16 days old) were used per treatment.

Both Table 6 and Table 7 shows that expression of a construct in transiently transformed soybean leaf tissue can be predictive for the level of expression of the same construct that is stably transformed into a soybean plant. In the examples provided in Table 6 and Table 7, the level of expression in the codon optimized HPPD was low when compared to expression of the non-codon optimized HPPD construct in both the soybean transient expression system of the present invention and in stably transformed soybean plants. Thus, the in planta transient expression system of this invention can be used to determine or predict if a particular construct will be successfully expressed at an optimal level in a stably transformed plant. The two different soybean in-planta transient expression systems described herein can be also used to test the expression of multiple nucleotide sequences. The multiple nucleotide sequences can be comprised in a single vector comprising the one or more nucleotide sequences. Alternatively, multiple vectors can be used with each vector comprising one or more nucleotide sequences to be expressed.

The advantage of the testing in the in planta transient expression system of the present invention is that significant resources can be saved by determining which constructs will work and which will not. If a construct does not work, adjustments can be made (e.g., nucleotide sequence position within the construct can be altered) and the construct tested again. Thus, the effectiveness of a construct can be tested for relatively low cost versus the expenditures related to stably transforming plants and then regenerating and growing the stably transformed plants up to a point at which expression levels can be tested.

The foregoing is illustrative of the present invention, and is not to be construed as limiting thereof. The invention is defined by the following claims, with equivalents of the claims to be included therein.

What is claimed is:

1. A method of transiently expressing one or more nucleotide sequences in one or more cells of an intact whole soybean plant, comprising:
    a) contacting the surface of an intact soybean leaf of a whole soybean plant with an abrasive;
    b) contacting the abraded soybean leaf and/or the whole soybean plant comprising the leaf with a solution comprising bacterial cells competent for nucleic acid transfer and a surfactant, wherein the bacterial cells comprise the one or more nucleotide sequence(s) to be transiently expressed, and wherein said bacterial cells are *Agrobacterium*, *Rhizobuim*, *Mesorhizobium*, or *Sinorhizobium* cells;
    c) applying a vacuum to the contacted soybean leaf of step (b) and/or the whole soybean plant comprising said leaf of step (b); and
    d) releasing the vacuum, thereby introducing the solution into the abraded soybean leaf,
whereby the one or more nucleotide sequences are transiently expressed in one or more cells of the soybean plant.

2. The method of claim 1, wherein the bacterial cells competent for nucleic acid transfer are *Agrobacterium* cells.

3. The method of claim 1, wherein the surfactant is selected from the group consisting of Silwet L-77®, Tween® 20, Triton® X-100, Sylgard 309®, and any combination thereof.

4. The method of claim 1, wherein said contacting in step (b) comprises immersing the abraded leaf and/or the whole soybean plant comprising said leaf in the solution.

5. The method of claim 1, wherein said abrasive comprises sandpaper.

6. The method of claim 1, wherein in step (a) the abaxial of the soybean leaf is contacted with the abrasive.

7. The method of claim 6, further comprising contacting the abaxial side of the leaf with alcohol prior to step (a).

8. The method of claim 7, wherein the alcohol is ethanol.

9. The method of claim 1, wherein the vacuum pressure is in a range from about 5 psi to about 30 psi and the time for applying the vacuum is about 30 seconds to about 5 minutes.

10. The method of claim 1, wherein step (c) and step (d) are repeated.

* * * * *